(12) United States Patent
Kindersley

(10) Patent No.: US 7,997,151 B2
(45) Date of Patent: Aug. 16, 2011

(54) AUTOMATED APPARATUS AND METHOD FOR DETERMINING PHYSICAL PROPERTIES OF MATERIALS

(76) Inventor: Peter G. Kindersley, Queensbury, NY (US)

(*) Notice: Subject to any disclaimer, the term of this patent is extended or adjusted under 35 U.S.C. 154(b) by 234 days.

(21) Appl. No.: 12/320,527

(22) Filed: Jan. 28, 2009

(65) Prior Publication Data

US 2009/0188330 A1   Jul. 30, 2009

Related U.S. Application Data

(60) Provisional application No. 61/006,714, filed on Jan. 29, 2008.

(51) Int. Cl.
*B25B 23/14* (2006.01)
(52) U.S. Cl. ........................ 73/862.21; 73/760
(58) Field of Classification Search .......... 73/7, 9, 73/862.21
See application file for complete search history.

(56) References Cited

U.S. PATENT DOCUMENTS

| | | | | |
|---|---|---|---|---|
| 4,691,576 A * | 9/1987 | Schleuniger et al. | ........... | 73/821 |
| 4,936,135 A * | 6/1990 | Annis et al. | ........... | 73/7 |
| 5,490,410 A * | 2/1996 | Markstrom | ........... | 73/9 |
| 5,900,531 A * | 5/1999 | Mani et al. | ........... | 73/9 |
| 5,955,655 A * | 9/1999 | Evans | ........... | 73/7 |
| 6,349,587 B1 * | 2/2002 | Mani et al. | ........... | 73/9 |
| 6,418,776 B1 * | 7/2002 | Gitis et al. | ........... | 73/10 |
| 6,615,640 B2 * | 9/2003 | Ahn et al. | ........... | 73/9 |
| 7,788,965 B2 * | 9/2010 | Arnold et al. | ........... | 73/9 |
| 2010/0037675 A1 * | 2/2010 | Hannahs et al. | ........... | 73/7 |

* cited by examiner

*Primary Examiner* — Max Noori
(74) *Attorney, Agent, or Firm* — Nixon & Vanderhye P.C.

(57) ABSTRACT

Automated apparatus and method to determine physical properties of materials as they are moved relative to each other while in contact are disclosed. Physical properties between materials of interest (e.g., galling resistance, coefficient of friction, and wear rate) are derived under a variety of conditions including dry unlubricated condition, at ambient and at extreme high and low temperatures, lubricated, or when submerged.

36 Claims, 7 Drawing Sheets

AUTOMATED APPARATUS AND METHOD FOR DETERMINING PHYSICAL PROPERTIES OF MATERIALS

RELATED APPLICATION

This application claims priority and benefit of U.S. provisional patent application 61/006,714 entitled "METALS GALLING TESTER" filed Jan. 29, 2008, which is incorporated herein by reference in its entirety.

BACKGROUND

1. Technical Field

Physical properties of materials (e.g., resistance to galling, coefficient of friction, and wear rate) as they are moved relative to each other while in contact are measured.

2. Related Art

Wear-resistant couples are used in literally thousands of applications in which the couples slide while in contact with each other. The vast majority of such wear-resistant couples are made from metals. However, some couples are made from ceramics or from mixtures that include some ceramics and other solid materials.

In the process of designing mechanical equipment made from materials such as metals and ceramics, it is important to have knowledge of suitable pairs of materials or material coatings that must move in contact with each other at a high level of contact pressure so that undesirable events such as galling may be prevented. Galling of metals, also referred to as "cold welding", is said to occur when one surface in contact adheres to the other surface with such strong adhesion that a part of one of the surfaces is torn away, and both surfaces become damaged. This phenomenon occurs at temperatures far below softening or melting point of metals, hence the term "cold welding".

Galling can occur between metal surfaces that are dry and unlubricated, or lubricated, or wetted by some fluid. Different pairs of metals moving in contact under a high level of stress have different resistance to galling, and the designer must select a metal pair that has a high enough degree of galling resistance, hereinafter referred to as "GR", to prevent damage to surfaces of the coupling parts.

A non-exhaustive list of areas in which knowledge of GR is important include:

Sleeve-type bearings, where shafts rotate in supporting sleeves, sometimes with considerable forces pressing the parts together;

Internal parts for valves, where the parts are forced together by high pressure gas or steam or liquid that the valves are containing, as they slide against each other while the valves are operated; and Material selection for nuts and bolts and machine screws, where there is sliding of contact surfaces of threads as the nuts, bolts, and/or screws are tightened, usually with high contact pressure.

There are thousands of similar industrial applications where GR between metal pairs is important to know, to assure reliable product designs. Knowledge of GR for couples is important to enable sound design.

It is also significant to have information on coefficient of friction, hereinafter referred to as "COF", of couples, so that inherent resistance of the material pair to slide, one on the other, is known. This knowledge allows a design in which adequate force is supplied to produce sliding motion required in the equipment under design. The COF can be defined as the force required to produce sliding between two parts held together in contact, divided by the force that is holding them together. Less force is required to produce sliding when COF is low. Thus, in some instances, selection of metal couples should be considered for adequate GR, and also for lowest, or at least adequately low, COF.

Considering the importance of having these types of knowledge, there is surprisingly limited information available in the technical literature on GR and COF between various load-bearing metal couples. This is true even for those that have been in common use for many years. In addition, new metal alloys, new galling resistant coatings, and coating methods are introduced every year. There is much information on their strength and hardness and bond strength. However, there is an almost complete lack of data on their GR or COF, when used in contact with themselves or in combination with large number of other alternatives. Examples include new metal carbide and metal nitride coatings that can be extremely useful in preventing wear and galling and in lowering friction between parts, but virtually no data is available for their threshold GR, i.e., the contact pressure at which galling commences for that particular couple, nor for their COF. There is also similar lack of information on wear rates, hereinafter referred to as "WR", of couples.

SUMMARY

The disclosed exemplary embodiments relate to method(s) and apparatus(es) for determining physical properties between materials of interest such as, e.g., GR, COF, and/or WR.

To determine GR of two materials, the exemplary embodiments move samples of materials to be in contact with each other with a known amount of thrust force. Samples are rotated against each other while in forced contact and subsequently inspected to determine GR.

In the exemplary embodiments, to determine COF, samples are moved to be in contact with each other with a known amount of thrust force. Then the torque required to rotate the materials is measured. The COF is calculated based on the applied thrust and torque.

In the exemplary embodiments, to determine WR, lengths of the materials are measured. Then, similar to determining GR, samples are moved to be in contact with each other with a known amount of thrust force, and are rotated against each other while in forced contact. Afterwards, the lengths of samples are again measured, and WR is calculated based on length reductions.

One exemplary embodiment of an apparatus arranged to determine physical properties between materials as they are moved relative to each other includes first and second members respectively arranged to secure first and second test samples and a controllable drive unit. Members can move with respect to one another so that the test samples come into contact with each other.

In this embodiment, the controllable drive unit linearly drives at least one member toward the other with a controlled magnitude of thrust force and rotates at least one member with respect to the other with a controlled magnitude of torque while the test samples are in contact. The drive unit can be a single unit or can be implemented as a combination of controllable linear and rotational drive units. One or both thrust and torque magnitudes are adjustably controllable.

In the exemplary embodiment, first member is hollow and extends along a longitudinal axis with second member coaxially received therewithin. Movement along and rotation about the axis is permitted. That is, second member is slidably and rotably received within first member with first and second test samples carried by these members at their distal ends coming into rotational sliding contact with controlled thrust and torque.

The exemplary apparatus includes a drive shaft coupled to and axially aligned with second member and also coupled to both linear and rotational drive units. In this manner, thrust and torque from the drive units can be applied to second member and ultimately to second test sample. When both torque and thrust are applied to second member, first member can be fixed in relation to the drive units, for example, by fixedly attaching to a frame assembly.

In an example aspect, both members secure samples in sample holders preferably located at respective distal end portions away from drive units. This conveniently allows distal end portions and carried samples to be projected into an environmental control chamber that does not contain the drive units. The chamber can be used to subject samples to extreme temperatures, high or low, or be used to immerse samples in liquids without subjecting the drive units to same extreme environments.

To further protect drive units from extreme temperatures, thermal impediment can be located between first member and frame assembly. The thermal impediment can be hollow and axially aligned with a hollow part of the first member.

The exemplary apparatus includes an attachment to allow an externally applied torque to rotate at least one member with respect to the other while test samples are in forced contact due to thrust applied by the linear drive unit.

Preferably, test samples are cylinders with common dimensions on at least their contacting end surfaces. Also preferably, the cylindrical test samples include a recess formed at a center portion of contacting end surfaces.

The exemplary apparatus provides for convenient testing of physical properties of materials of interest including metals and other wear-resistant solid material couples under a variety of conditions including dry unlubricated conditions, at ambient and at extreme high and low temperatures, lubricated, or submerged in liquids. Significantly, the exemplary apparatus provides these and other advantages in a self-contained, all inclusive bench-top equipment.

BRIEF DESCRIPTION OF THE DRAWINGS

The foregoing and other objects, features, and advantages of the invention will be more apparent from the following more particular description of exemplary embodiments as illustrated in the accompanying drawings in which reference characters refer to the same parts throughout various views.

DETAILED DESCRIPTION OF EXEMPLARY EMBODIMENTS

Figure 1:
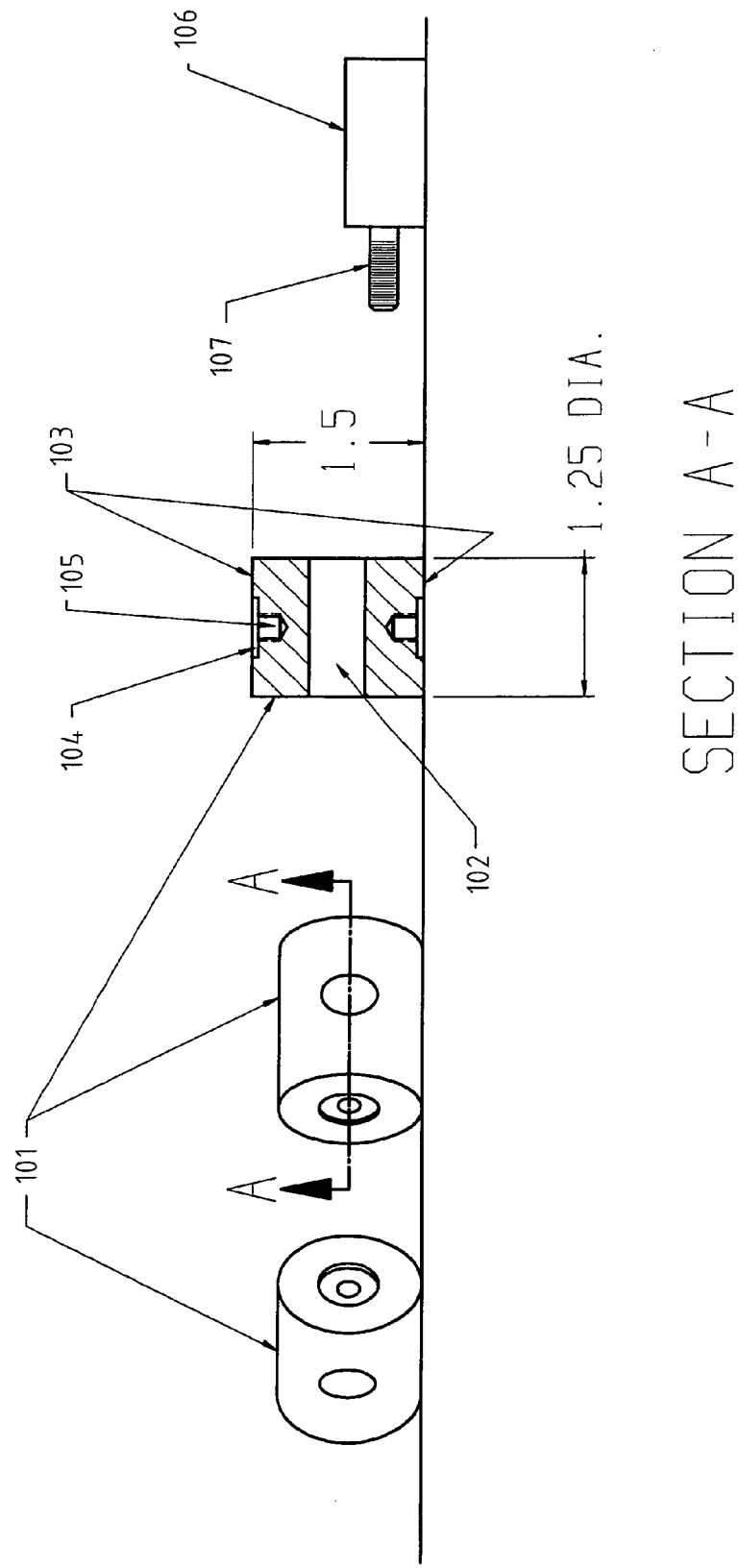
FIG. 1 illustrate multiple views of typical test samples, and a tool for inserting and removing samples in and out of an apparatus.

In the following description, for purposes of explanation and not limitation, specific details are set forth such as particular architectures, interfaces, techniques, and so on. However, it will be apparent that the technology described herein may be practiced in other embodiments that depart from these specific details. That is, those skilled in the art will be able to devise various arrangements which, although not explicitly described or shown herein, embody the principles of the described technology.

In some instances, detailed descriptions of well-known devices, circuits, and methods are omitted so as not to obscure the description with unnecessary detail. All statements herein reciting principles, aspects, embodiments and examples are intended to encompass both structural and functional equivalents. Additionally, it is intended that such equivalents include both currently known equivalents as well as equivalents developed in the future, i.e., any elements developed that perform the same function, regardless of structure.

Due to the preponderance of metal couples, present discussion concentrates on metal couples. But it should be understood that the discussion also applies fully to non-metallic and partly metallic couples including ceramics, carbides, and so on.

As noted, there is surprisingly very little data available in the technical literature on physical properties such as GR, COF, WR, etc. between various load-bearing couples, even for couples that have been in common use for many years. In addition, new materials such as metal alloys and ceramics for load-bearing applications are being continually introduced, and there is very little data for these as well.

Because of the absence of information in technical literature, persons that have a need to know historically have had to do their own testing, or they have contracted with a testing laboratory. This has resulted in an immense amount of duplication of effort worldwide, because testers have unknowingly repeated hundreds of tests that others have done elsewhere.

For GR, one of the reasons for there being such limited information worldwide is perhaps that there has been only one well known standard test procedure for GR, namely that published by The American Society For Testing Of Materials, also referred to as "ASTM", and it has not been completely adequate or universally accepted. ASTM's longstanding basic testing method has been to force the end of a small diameter cylinder made from one material sample against a flat plate made from another material sample, typically in a press, and to rotate the cylinder through a single revolution.

Recently, the ASTM procedure has been abandoned in favor of a new procedure due to a recognition that ASTM testing with a cylinder and plate can produce false and unreliable test results. When an end of a cylinder is pressed against a larger flat plate, there is an inherent stress concentration the around outer edge of the cylinder, making actual contact stress there considerably larger, by as much as 400% more, than is calculated by simply dividing applied force by area of the cylinder end. There are other shortcomings of the ASTM test procedure. These include one or more of the following:

Previous data accumulated over decades of testing is now suspect—evidenced by the fact that supposedly identical tests have produced numerical GR results that vary by as much as 300%;

Not suitable for testing other than at ambient temperature—little data being available regarding high or low temperature effects on galling;

Not suitable for testing in the presence of liquids—little data being available regarding liquid effects;

Not suitable for testing with a large number of revolutions—little data being available regarding prolonged force application effects;

Requires a press or other large equipment to produce the contact force needed—test typically not conducted with equipment that is self-contained; and Requires constant human effort and involvement—the test is expensive.

These and other shortcomings have limited acceptability and use of the standard, and therefore the accumulation of data for GR has been hampered. The foregoing shortcomings have also hampered data accumulation for COF and WR of wear couples.

In the new procedure, which has been embraced by ASTM, ends of two cylindrical samples of same diameter are pressed together. When two ends of same diameter are pressed together, force is applied evenly over surfaces of the cylinder ends. However, note that some of the shortcomings related to the ASTM procedure may also apply to the new procedure.

These and other shortcomings of known test procedures are addressed by one or more exemplary embodiments described below.

FIG. 1 provides multiple views of exemplary test samples 101, which are also referred to as "coupons". As seen, each test sample 101 is a cylinder with predetermined diameter (e.g. approximately 1.25") and predetermined length (e.g. approximately 1.5"). For the remainder of this document, test samples are assumed to be cylindrically shaped unless specifically stated otherwise. Therefore, terms "sample", "cylinder", and "coupons" will be used interchangeably. Preferably, diameters of both cylinders 101 match. Each cylinder 101 includes a centrally located transverse through hole 102 with a predetermined diameter (e.g. approximately 0.50").

During testing, end surfaces 103 of cylinders 101 are engaged, i.e., are in contact with each other. Thus, for each cylinder 101, one or both end surfaces 103 are prepared for testing. When both end surfaces 103 are prepared, cylinder 101 can accommodate two separate tests. In one aspect, preparation includes forming cylinders 101 themselves from materials of interest. Alternatively, end surfaces 103 of the samples 101 may be coated with materials of interest.

Engaged end surface 103 of at least one cylinder 101—preferably both—are formed to include a shallow recess 104 of a predetermined diameter (e.g. ½") located in a center of the end surface 103. The end surface center area experiences only limited relative movement (e.g., almost none at the center point) and that could compromise the validity of the test result if not removed. The diameter of the recess 104 is selected so that there is meaningful movement of all surface area in contact.

FIG. 1 also illustrates an exemplary tool 106 that can be used to insert cylinders 101 into a test apparatus to determine physical properties. To facilitate installation and removal of cylinders 101 in and out of the apparatus, one or both ends of cylinder 101 include(s) a shallow central female threaded hole 105 of a predetermined diameter (e.g. ⅛"). Tool 106 includes a rod with a male thread 107 that matches the threaded hole 105. The thread 107 can be screwed into the hole 105 so that cylinders 101 can be held while they are inserted into and removed from the test apparatus.

Figure 2:
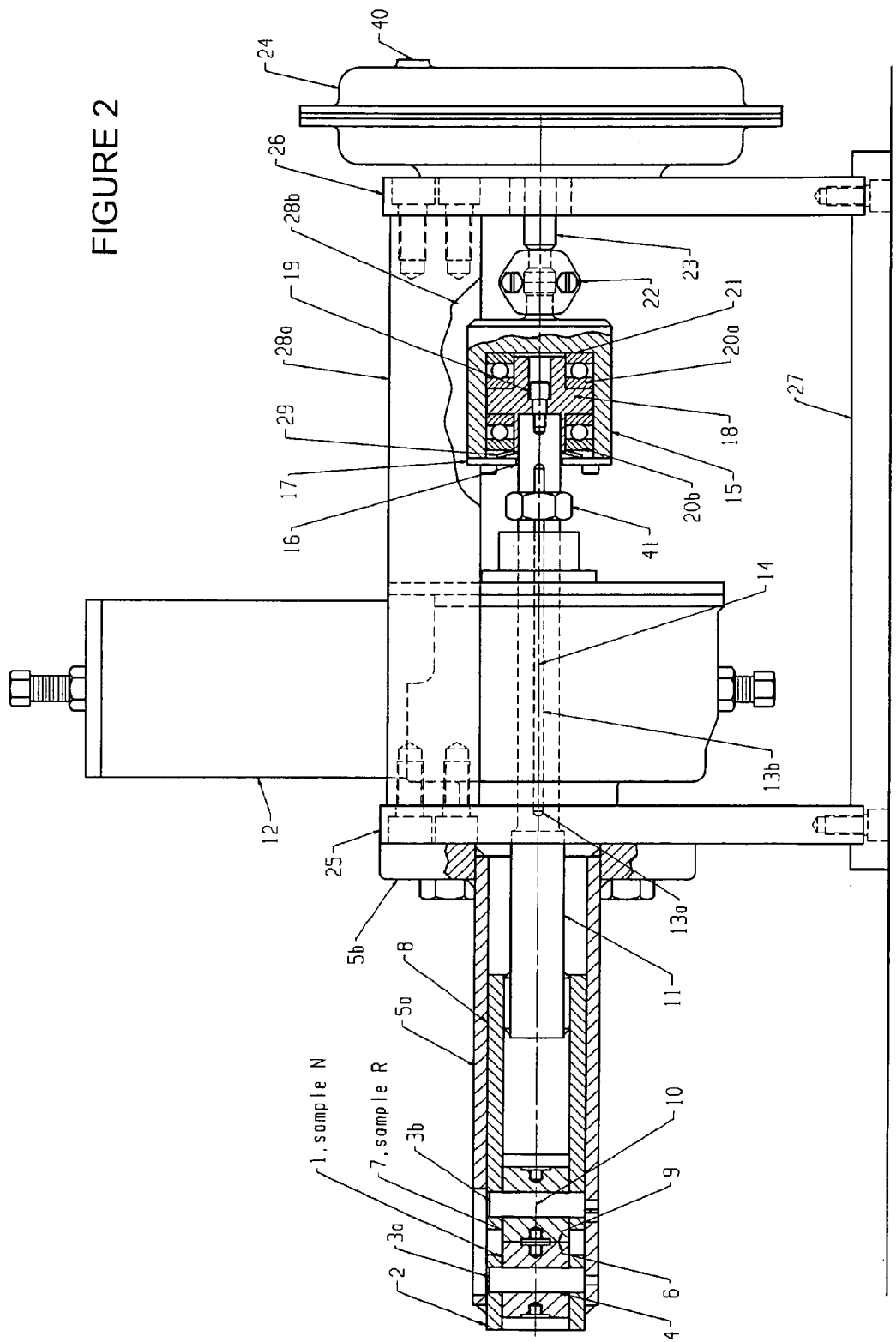
FIG. 2 illustrates a first exemplary embodiment of an apparatus arranged to determine physical properties between test samples.

FIG. 2 illustrates a first exemplary test apparatus arranged to determine physical properties—e.g., GR, COF, and/or WR—between test samples. The apparatus includes a first member 5a arranged to secure a first test sample N, a second member 8 arranged to secure a second test sample R, and a controllable drive unit arranged to apply controlled magnitudes of thrust and torque. The controllable drive unit may be implemented as a single unit or as a combination of drive units 24, 12 separately providing thrust and torque. Apparatus can include a vertical plate 25, which is a part of a frame assembly 25, 26, 27 supporting the apparatus. For simplicity, reference 25 will also be used to reference the frame assembly.

Unless specifically stated otherwise, it can be assumed that both samples N, R are cylindrical as illustrated in FIG. 1 and prepared with materials of interest. Thus, they may also be referred to as cylinders N, R. Also unless specifically stated otherwise, it may be assumed that engaging end surfaces 6, 9 of cylinders N, R—i.e. end surfaces that in contact—are dimensionally the same.

First and second members 5a and 8 are arranged so that they can move relative to each other, which allows engaging surfaces 6, 9 of cylinders N, R to contact each other. First member 5a can be hollow and extend along a longitudinal axis. Second member 8 can be coaxially received within first member 5a so that relative movement along and a rotation about the axis is permitted.

Relative movements between members 5a, 8 are provided by the controllable drive unit, which, in one variant, can be implemented as a combination of a controllable linear drive unit 24 and a controllable rotational drive unit 12. Linear drive unit 24 is arranged to drive at least one member 5a, 8 towards the other member 8, 5a with controlled magnitude of thrust. Rotational drive unit 12 is arranged to rotate at least one member 5a, 8 with respect to the other member 8, 5a with controlled magnitude of torque. Member 5a, 8 being driven by drive unit 24 can be the same as or different from member 5a, 8 being driven by drive unit 12. The drive units will be described in further detail below.

As illustrated in FIG. 2, first member 5a can be implemented as an elongated outer pipe 5a with a flange 5b formed at a proximal end portion thereof—i.e., end portion of pipe 5a closer to frame assembly 25 and the drive units 12, 24. Flange 5b, which can be integrally formed with pipe 5a, fixes pipe 5a to frame assembly 25. An inner end surface 6 of cylinder N, as mounted, will have been prepared for GR, COF, and/or WR testing, and is formed of either a base material of interest, or is a coating of interest that is to be tested.

Second member 8 can also be implemented as an elongated inner pipe 8 that is slidably and rotationally received within outer pipe 5a. As arranged, cylinder R secured to second member 8 can be moved to be in contact with cylinder N secured to first member 5a. Cylinder R is also prepared with a material of interest, which can be same or different from the material of interest of cylinder N.

While FIG. 2 shows that first member 5a is fixed to frame assembly 25, this is not strictly necessary. It is only necessary that relative movement between members 5a, 8 is allowed so that cylinders N, R can come into contact and be rotated while in contact. Thus, one or both members 5a, 8 can be arranged to move relative to frame assembly 25.

Members 5a, 8 respectively include first and second sample holders arranged to secure samples N, R so that they are fixed to their respectively associated members. First sample holder can be implemented as a combination of inner fixed pipe 2 and pin 3a as illustrated in FIG. 2. Sample N is mounted in pipe 2 by pin 3a, which can be formed from a strong metal, that is passed through a centrally located hole 4 (same as the transverse hole 102 in FIG. 1) drilled through sample N and through matching holes in pipe 2. Inner fixed pipe 2 is fixedly attached to outer fixed pipe 5a, for example, through welding. For simplicity, reference "3a" will be associated with first sample holder hereinafter unless specifically stated otherwise.

Second sample holder can be implemented also as pin 3b arranged to mount second sample R to movable inner pipe 8 through matching holes in pipe 8, which is in a similar manner to mounting sample N to outer pipe 5a.

As noted, samples N, R are preferred to be the same dimensionally, at least for engaging end surfaces 6, 9. In FIG. 2, inner fixed pipe 2 is shaped similarly to inner movable pipe 8, i.e., has the same diameter, and is also fitted within outer pipe 5a. This maximizes the chance that a matching contact will be established between engaging end surfaces 6, 9 of samples N, R. This is one of several ways to accomplish this purpose.

Pins 3a (first sample holder) and 3b (second sample holder) can be slightly enlarged in center areas 10 thereof, e.g., by simple crowned machining. This allows samples N, R to rock slightly in position allowing their engaging end surfaces 6, 9 in contact to be positioned flatly against each other.

Sample holders 3a, 3b are both positioned at distal end portions of members 5a, 8, i.e., at end portions located away from frame assembly 25 and from drive units 12, 24 as illustrated in FIG. 2. While sample holders 3a, 3b can be positioned anywhere along their respective members 5a, 8, distal end portions are preferred for reasons explained below.

Physical properties information including GR, COF, and WR is important to have for couples operating at ambient temperatures. But in addition, it is also important to have information for products that operate at elevated temperatures, such as valves, or blowers, operating in contact with high temperature gases or steam or various molten materials. Similarly, there are equipments that must operate at very low temperatures, such as in equipment for the space program, and for equipment operating at cryogenic temperatures.

It is known that properties such as GR, COF, and/or WR of materials may change at elevated or at very low temperatures. Thus numerical evaluation for these properties of materials only at room temperature may not be sufficient information for design in cases of elevated temperatures or at very low temperatures, where couples may be required to operate in critical applications. As an example, there is virtually no generally available data for the GR, COF, and/or WR of couples at very high or at very low temperatures.

Similarly, there are occasions in which properties of materials operating in liquids is important such as for valves operating in contact with liquids in pipelines for example. Again, there is virtually no generally available data.

Figure 4:
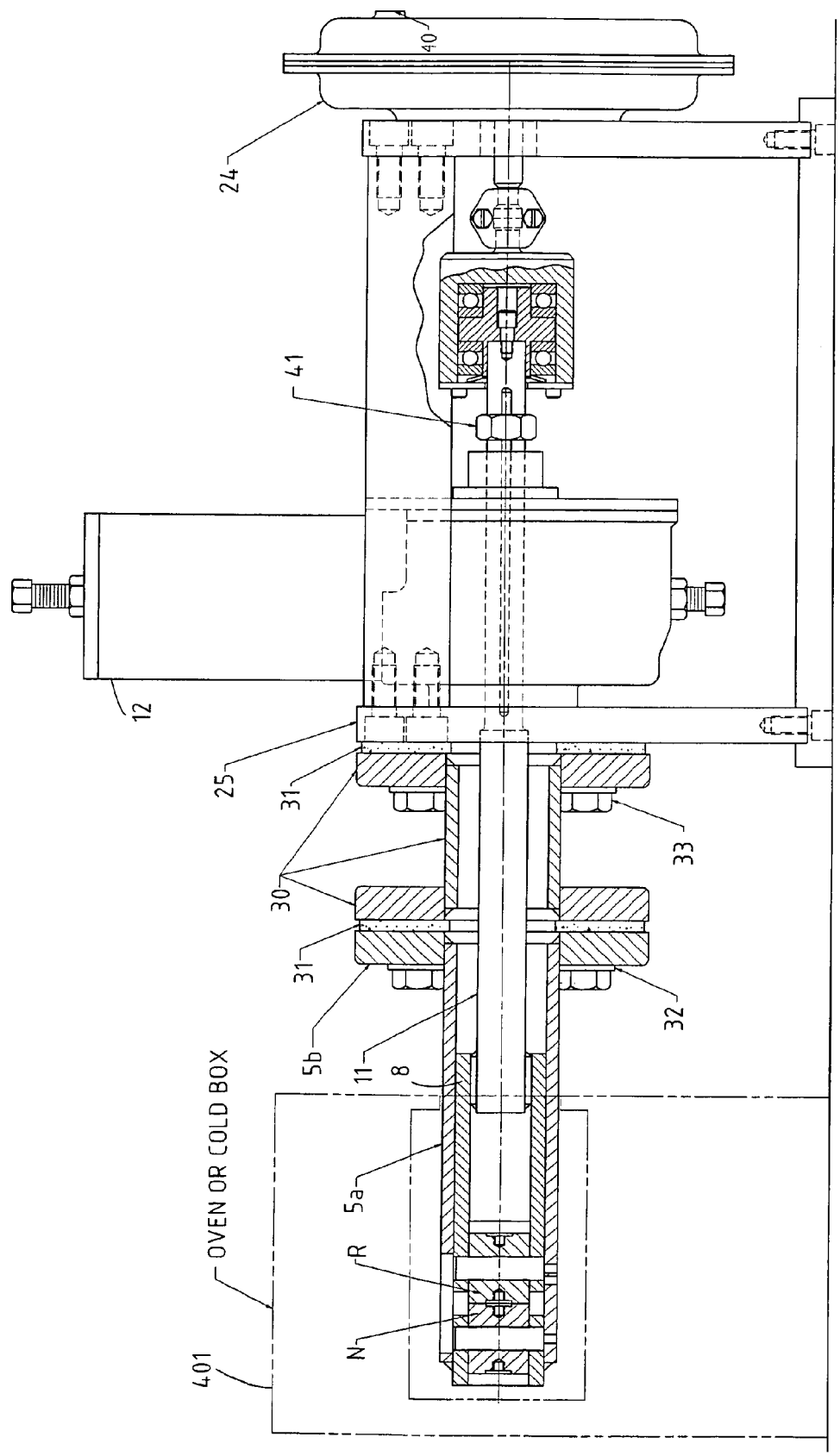
FIG. 4 illustrates a third exemplary embodiment of an apparatus arranged to determine physical properties between test samples in which test samples are subjected to extreme temperatures.
Figure 5:
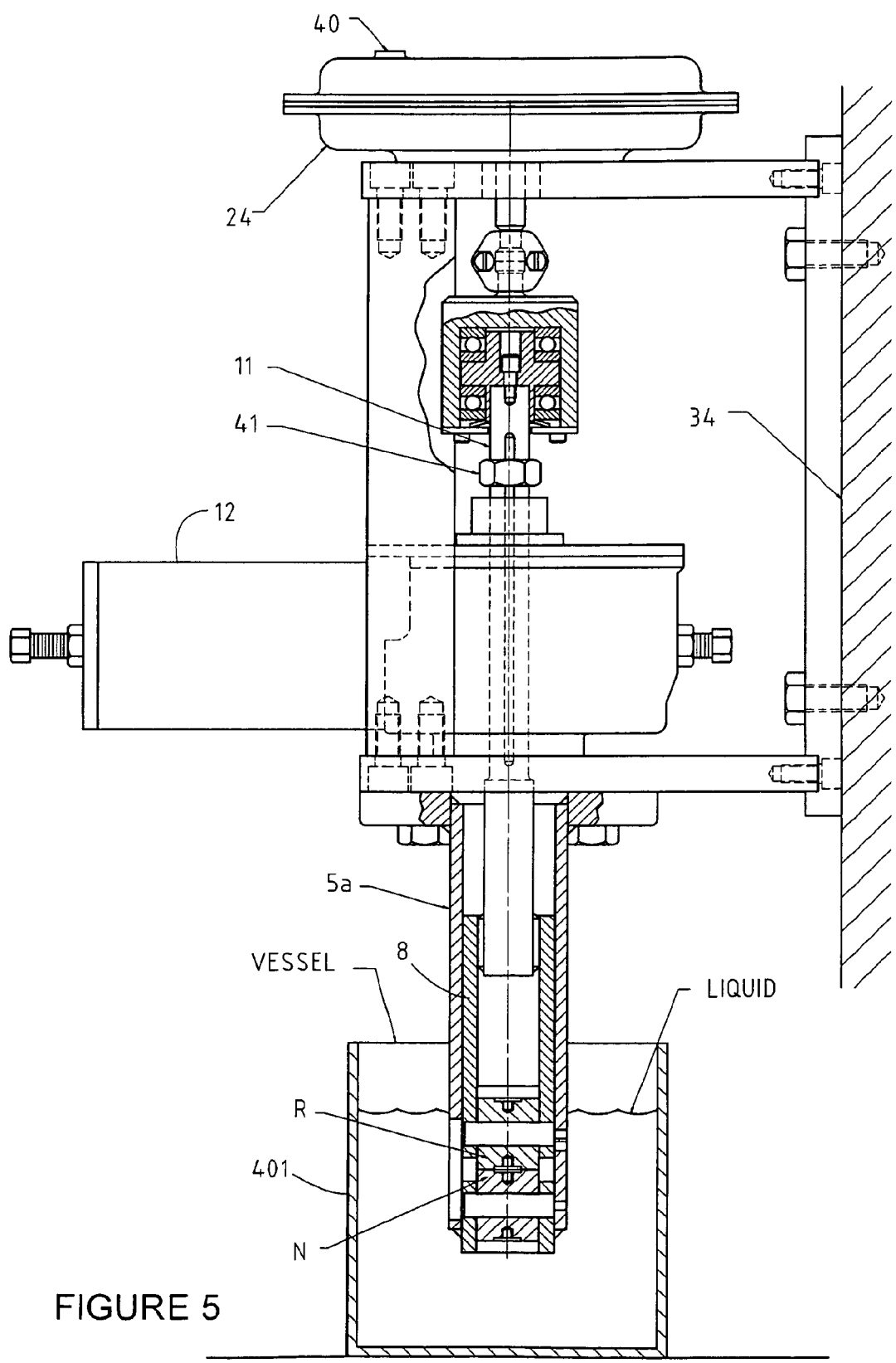
FIG. 5 illustrates a fourth exemplary embodiment of an apparatus arranged to determine physical properties between test samples in which test samples are subjected to a liquid.

As illustrated in FIG. 4, when sample holders are positioned at distal end portions of members 5a, 8, these end portions can be projected into an environmental control chamber 401 that does not contain the drive units 12, 24. Samples N, R can be inserted into chamber 401 while avoiding subjecting the drive units 12,24 and other working parts of the apparatus to extreme environment within chamber 401. Chamber 401 can be an oven or a cold-box to expose samples N, R to non-room temperature environment. In FIG. 5, distal end portions are projected into in a liquid environment contained within chamber 401 so that samples N, R are immersed in liquid.

To further protect drive units 12, 24 from being subjected to thermal extremes, the exemplary apparatus includes a thermal impediment 30 adapted to impede thermal transfer between distal end portions of members 5a, 8 and drive units 12, 24. Thermal impediment 30 includes low thermal conducting first and second gaskets 31 installed at both distal and proximal end portions thereof. Thermal conductivities of gaskets 31 are lower than both first member 5a and frame assembly 25. In so doing, effective thermal conductivity of impediment 30 is lower than first member 5a and frame assembly 25.

Thermal impediment 30 can be permanent. Preferably however, impediment 30 is detachably attached. In FIG. 2, proximal portion of first member 5a, without impediment 30, is attached to frame assembly 25. In FIG. 4, thermal impediment 30 is attached to frame assembly 25 and proximal portion of first member 5a attached to thermal impediment 30. As seen, impediment 30 is hollow and axially aligned with a hollow part of first member 5a so that second member 8 remains slidably and rotationally received within first member 5a. A longer shaft 11 (described in further detail below) is used (compare FIGS. 2 and 4) to accommodate added length due to impediment 30. In another variant, longer second member 8 (not shown) can be used so that shaft 11 need not be exchanged to accommodate added length when thermal impediment 30 is attached. Longer second member 8 would also be slidably and rotationally received within thermal impediment 30.

It is noted above that relative movements between members 5a, 8 are provided by the controllable drive unit, which can be implemented as a combination of linear drive unit 24 and rotational drive unit 12. In one variant, linear drive unit 24 is implemented as a diaphragm actuator 24 as illustrated in FIG. 2. To power actuator 24, compressed air is applied through a connection 40 of actuator 24. This causes inner pipe 8 (second member) to move longitudinally towards distal end portion of relatively fixed outer pipe 5a (first member). Magnitude of thrust is adjusted by adjusting the applied air pressure.

In detail, inner pipe 8 is attached to shaft 11, which passes slidably through a rotary actuator 12 (rotational drive unit). Shaft 11 has a keyway slot 13a and a square key 14 that engages in a matching keyway slot 13b in a bore of the rotary actuator 12. Shaft 11 enters a cylindrical bearing assembly 15 at an opening 16 in an end cap 17 of the bearing assembly 15, and then into a flanged tee-head 18 that is inside bearing assembly 15, and is bolted to tee-head 18 by a bolt 19 into an end of shaft 11. Tee-head 18 touches a ball-type thrust bearing 20a which in turn rests against an internal flat surface 21 in bearing assembly 15. The bearing assembly 15 is attached by a coupling 22 to a stem 23 of diaphragm actuator 24.

Applying compressed air through connection 40 causes a stem 23 to extend out of actuator 24 with an adjustable force, depending on the air pressure applied. This force is transmitted through coupling 22 to bearing assembly 15, which in turn transmits force through internal surface 21 to thrust bearing 20a, tee-head 18, and to an end of shaft 11. That force is transmitted along shaft 11, to inner pipe 8, then to sample R secured to inner pipe 8 towards sample N secured to outer pipe 5a. In the end, the thrust applied from drive unit 24 is applied to second member 8 (and thus, applied to sample R) through shaft 11. In the embodiment of FIG. 2, shaft 11 is axially aligned to and coupled to the proximal end portion of second member 8 and is also coupled to linear drive unit 24.

While drive unit 24 is shown to be a pneumatic device in FIG. 2, drive unit 24 can also be powered by a variety of sources including electric, hydraulic, mechanical, and so on in which the applied power can be adjustably controlled. Also, drive unit 24 can be powered by a combination of power sources.

Figure 3:
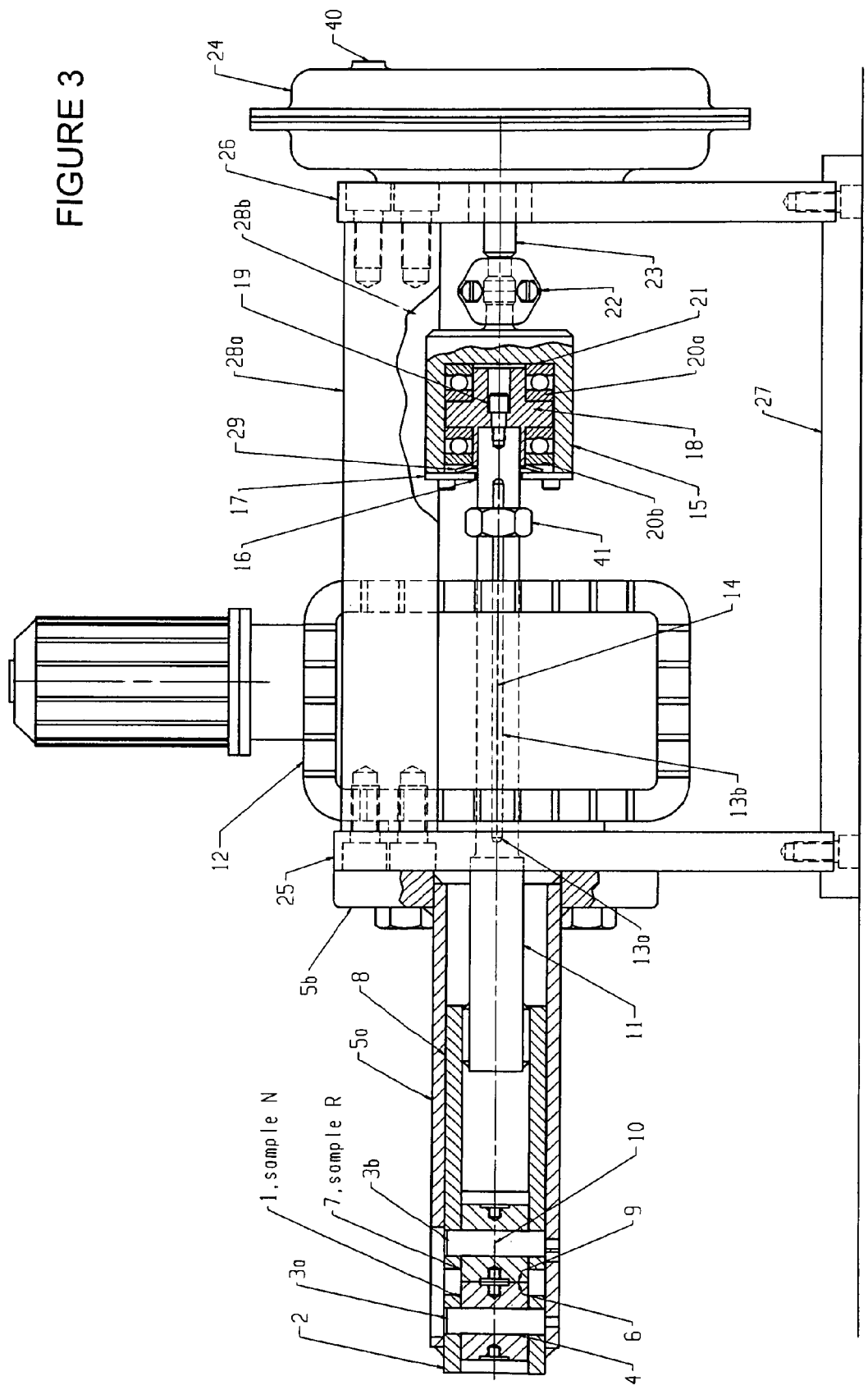
FIG. 3 illustrates a second exemplary embodiment of an apparatus arranged to determine physical properties between test samples.

Rotational drive unit 12 can be implemented as a pneumatic actuator 12 as illustrated in FIG. 2 or an electric actuator 12 as illustrated in FIG. 3. When power is applied to rotate the rotary actuator 12, one or both members 5a, 8 rotate with respect to each other. Rotation can be applied when samples N, R are in forced contact by thrust from linear drive unit 24.

Shaft 11 is also coupled to drive unit 12. Thus, torque applied by drive unit 12 is applied to second member 8 (and thus, also to sample R) through shaft 11. In detail, inner pipe 8 can be attached to shaft 11, which passes slidably through rotary actuator 12. Keyway slot 13a and square key 14 of shaft 11 that engages matching keyway slot 13b in a bore of rotary actuator 12 allows shaft 11 to be rotated by actuator 12.

Pneumatic actuator 12 in FIG. 2 is an example of a reciprocating actuator that rotates one of the members 5a, 8 back and forth over an arc typically of less than 360°. As illustrated, compressed air can be applied alternately to ends of the cylinder of pneumatic actuator 12, so that it reciprocally rotates one member back and forth through an arc of 90° for example. This is useful for testing with reciprocal rotation. For testing with continuous rotation, i.e. over many revolutions, electric actuator 12 illustrated in FIG. 3 may be used. Applying power to electric actuator 12 turns one of samples N, R continuously against the other.

While electric and pneumatic devices are shown, rotational drive unit 12 may be powered through other sources including hydraulic, mechanical, and so on in which the applied power can be adjustably controlled. A device with a combination of power sources is also contemplated. Regardless of the power source, drive unit 12 may be capable of supplying reciprocal or continuous rotation, or both as the need arises.

In a further detail of FIG. 2, to assure rolling rather than sliding rotary motion that could create fine metal particles inside bearing housing 15, a second thrust bearing 20b is located in bearing housing 15, disposed between tee head 18, which rotates, and a Belleville washer 29, which remains stationary. Belleville washer 29 is disposed between second bearing 20b and bearing housing cap 17. Strength of the Belleville washer 29 is selected so that two bearings 20a and 20b and tee head 18 are always held in gentle compressive contact between inner bearing housing surface 21 and bearing housing end cap 17. It is sufficient that the strength of Belleville washer 29 be slightly greater than force needed to retract shaft 11 slidably through rotary actuator 12.

Moreover, outer fixed pipe 5a can be mounted by flange 5b to vertical plate 25 of the whole frame assembly, which also includes another vertical plate 26, a base plate 27, and front and rear rectangular tie bars 28a and 28b that hold vertical plates 25 and 26 in place. Rotary actuator 12 can be mounted to the opposite side of vertical plate 25 and in alignment with flange 5b. Actuator 24 can be suitably mounted to vertical plate 26.

As noted, exemplary embodiments of the apparatus described thus far can be used to determine physical properties including GR, COF, and/or WR of materials. When determining GR, linear drive unit 24 drives members 5a, 8 toward each other to cause test samples N, R to be in contact with a controlled amount of force. Then rotational drive unit 12 rotates one of samples N, R with respect to the other while samples are in forced contact. Rotational drive unit 12 is adapted to (a) continuously rotate at least one member 5a, 8 with respect to the other over 360° and (b) reciprocally rotate, i.e., rotate back and forth, at least one member with respect to the other over an arc of less than 360°.

When determining COF of materials, linear drive unit 24 drives members 5a, 8 toward each other so that test samples N, R are in contact with a known amount of force. Then rotational drive unit 12 applies torque to rotate one of samples N, R with respect to the other while samples are in forced contact. Torque required to rotate the samples is measured or otherwise determined. As an example, torque can be determined by determining minimum power (pneumatic, electric, hydraulic, and so on) applied to rotational drive unit 12 required to barely turn sample R against sample N. Between torque and thrust, COF can be easily calculated.

Alternatively to determine COF, torque can be provided externally. In FIG. 2, apparatus optionally includes an attachment 41 that allows torque to be applied from an external source. Externally applied torque can rotate at least one member 5a, 8 with respect to the other 8, 5a while samples N, R and are in forced contact with each other due to thrust applied by linear drive unit 24. This may be useful in situations where externally applied torque can be more precisely measured relative to torque from rotational drive unit 12.

Apparatus can also be used to determine WR of materials. To test WR, lengths of samples N, R are measured before and after subjecting them to torque while in forced contact. After initial length measurement, linear drive unit 24 drives members 5a, 8 toward each other to cause test samples N, R to be in contact with a controlled amount of force. Then rotational drive unit 12 rotates one of samples N, R with respect to the other while samples are in forced contact. Rotational drive unit 12 is adapted to (a) continuously rotate at least one member 5a, 8 with respect to the other over more than 360° and (b) reciprocally rotate at least one member with respect to the other through a predetermined arc. Afterwards, length reduction is measured and WR is calculated.

Figure 7:
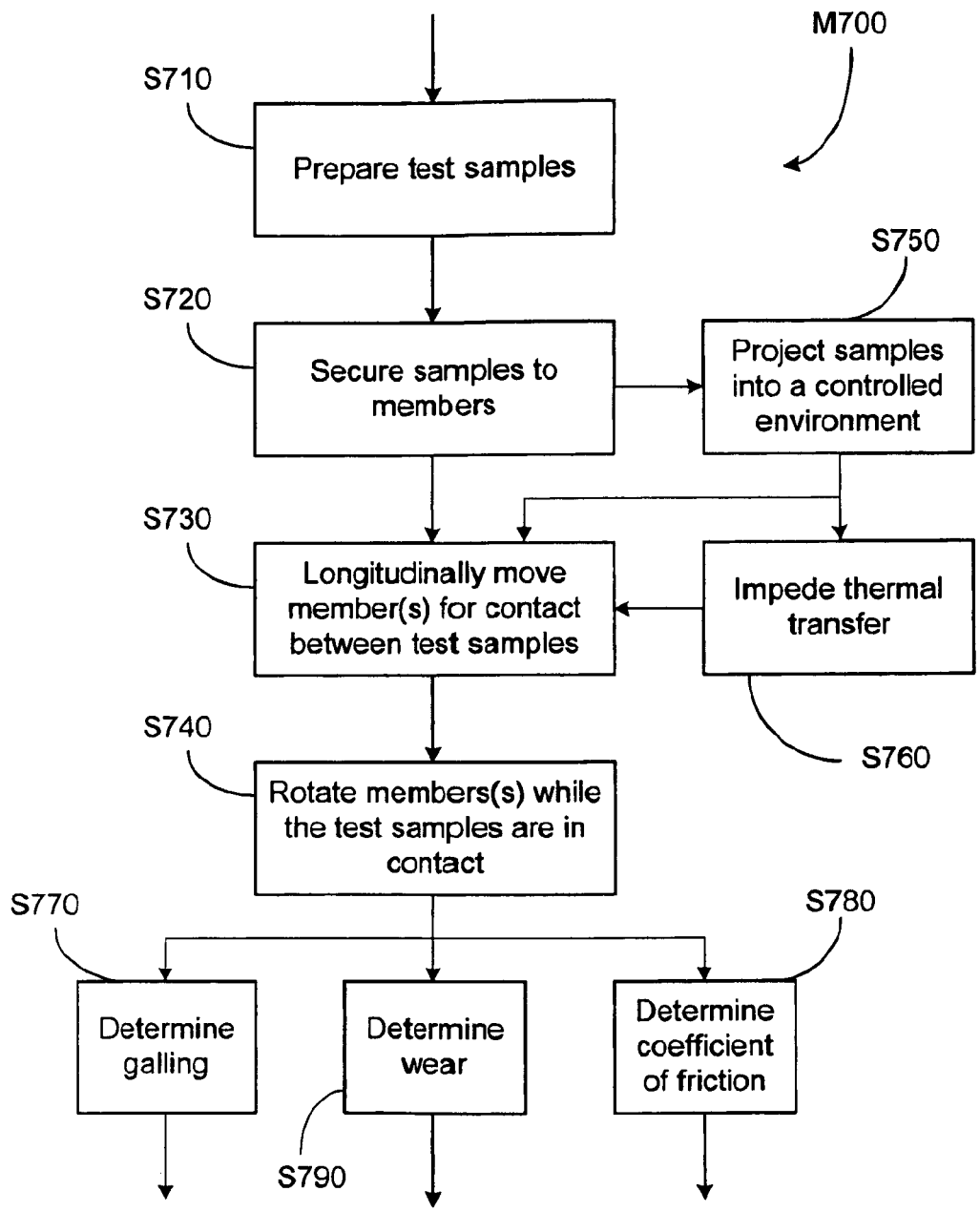
FIG. 7 illustrates an exemplary method to determine physical properties between test samples.

FIG. 7 illustrates an exemplary test method M700 for determining physical properties of sample materials. Here samples N, R are prepared in step S710. For example, a recess can be formed in center of an engaging end surface of one or both test samples N, R. Also, if samples themselves are not the materials of interest, then materials of interest can be coated to one or both engaging end surfaces of samples. In step S720, prepared samples N, R are secured respectively to members 5a, 8. Preferably, samples N, R are secured to distal end portions of members 5a, 8.

After securing samples to members, using linear drive unit 24, at least one member 5a, 8 is longitudinally moved toward the other member 8, 5a so that the engaging surfaces of samples N, R are in contact with each other with a controlled magnitude of linear thrust in step S730. In one aspect, proximal end portion of one or both members are moved.

In step S740, at least one member 5a, 8 is rotated with respect to the other member 8, 5a using rotational drive unit 12 to effect sliding rotational motion between test samples with a controlled magnitude of rotational torque.

For testing with reciprocal rotations, drive unit 12 can apply many cycles back and forth movements through an arc of less than 360°, e.g., 90°. For testing with continuous rotation, drive unit 12 can rotate samples through many revolutions. As will be appreciated, rotational drive unit 12 also might be started before or concurrently with initiation of thrust force.

After many rotations or cycles, samples N, R can be evaluated for GR in step S770, e.g., by inspection of test surfaces 6 and 9. To inspect the surfaces when the apparatus illustrated in FIG. 2 is used, air pressure is vented from diaphragm actuator 24 at air connection 40, and internal springs (not shown) in actuator 24 cause stem 23 to retract back into actuator 24. The retraction is transmitted through coupling 22 to bearing assembly 15, which causes screw 19 to pull on shaft 11, causing it to retract, causing sample R to be retracted. Samples N and R become loose on pins 3a and 3b, so that they can be removed, for inspection of tested surfaces 6 and 9.

Samples N, R can be evaluated for COF in step S780. For COF determination, magnitudes of both the linear thrust and rotational torque required to rotate at least one test sample while subjected to linear thrust are measured. In a simple case, magnitude of thrust is controlled, and therefore, is already known and it is thus only required to measure torque, which can be applied by either rotational drive unit 12 or from an external source through attachment 41.

In step S790, samples N, R can be evaluated for WR. To test WR of the materials being tested, lengths of the material samples are first measured precisely, before being secured to the test apparatus. For example, this can be a part of step S710 of preparing samples N, R. Samples are then secured in the test apparatus, an appropriate thrust magnitude is exerted and one sample is rotated against the other a large number of counted times in steps S730 and S740. Then in step S790, sample lengths are re-measured precisely. WR can be calculated based on length reduction of samples.

If samples are to be subjected to a controlled environment such high or low temperatures or a liquid, then prior to performing steps S730 and S740, end portions of members 5a, 8 which hold samples N, R are projected into an environmentally controlled unit in step S750. Additionally, a thermal transfer can be impeded between distal and proximal end portions of members 5a, 8 in step S760 so as to protect drive units 12, 24 from being subjected to extreme temperatures.

Figure 6:
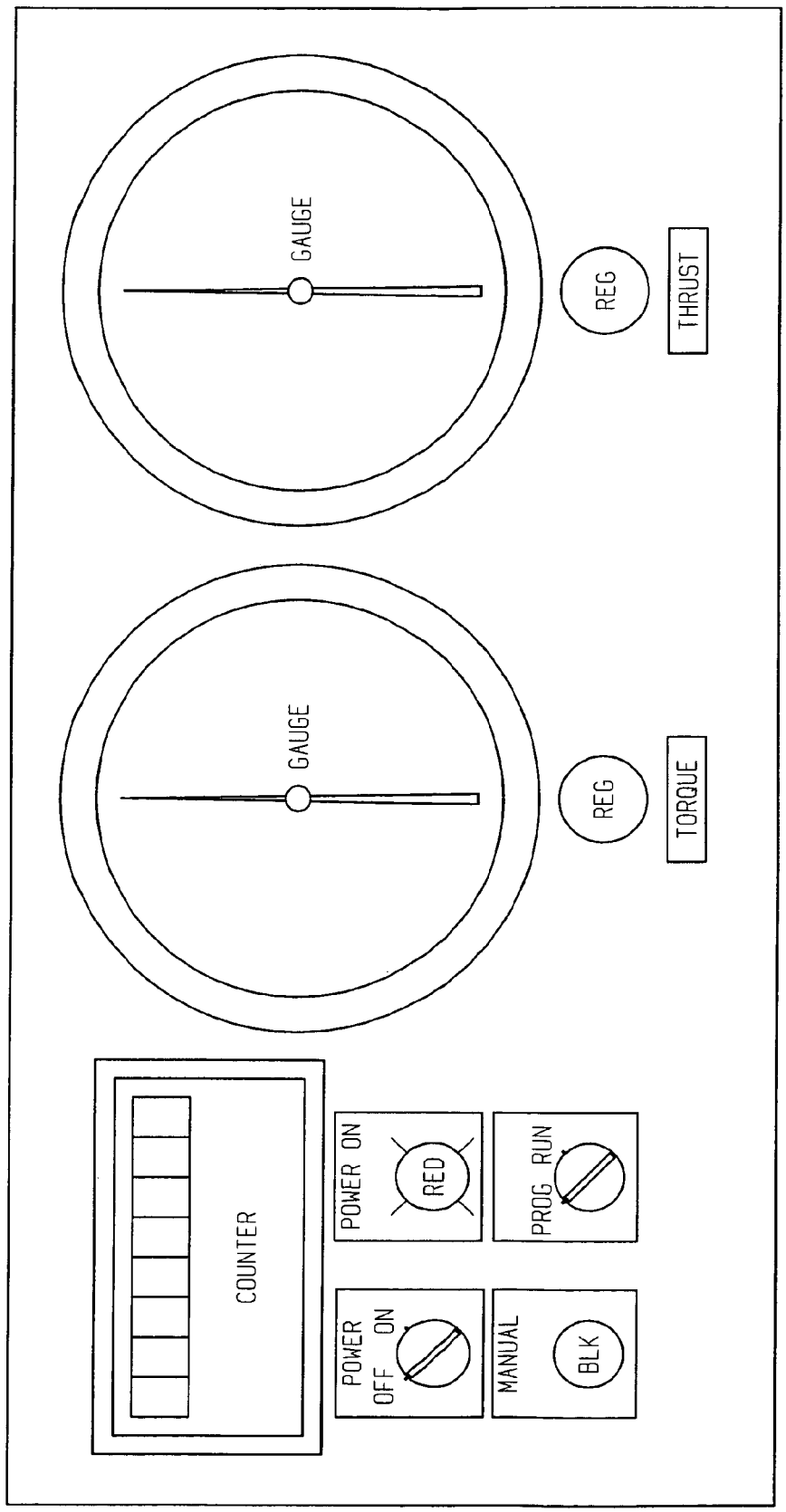
FIG. 6 an exemplary embodiment of a control panel for use with the apparatus.

When it is desired to test GR or WR of samples over many rotations or cycles, apparatus may be connected to an automatic control panel as illustrated in FIG. 6. Alternatively, control panel may be included as a part of the test apparatus.

Rotational drive unit can be equipped with position switches, for example, one at each end of the stroke for a reciprocating type unit, or one at the 0° start position for a continuous rotation type unit. Number of rotations or cycles desired for test is set on a presettable counter, and appropriate power level, e.g., air pressure level, and connected to linear drive unit 24 at connection 40. A switch in control panel is turned to "RUN" position. A control circuit then applies power to rotational drive unit 12, and apparatus rotates or cycles back and forth until preset number of rotations or cycles have completed and counter has counted down to zero. Power is then removed from rotational drive unit 12 automatically by control circuit, and apparatus stops operating. Inspection of test surfaces 6 and 9 is then conducted as described above.

For convenience, control panel may also contain a power regulator for linear drive unit 24, and also a regulator for rotational drive unit 12, if such is used. Control panel may also contain lights and switches required for safe operation.

The disclosed exemplary apparatus and method provides for convenient, fast, reliable determination of physical properties (GR, COF, WR, etc.) of materials overcoming at least same shortcomings of past procedures and equipment. Advantages may include:

Apparatus can be a self-contained automatic bench-top testing machine;

Apparatus is simple and easy to use;

Apparatus can be automatic, when operated in conjunction with a presettable counter that can be preset for a large number of rotations or reciprocating cycles, allowing unattended operation with automatic shutoff after the preset rotations or cycles have been completed;

Apparatus uses inexpensive cylindrical test sample coupons, placed end to end;

Apparatus allows determining physical properties at elevated temperatures, up to 1800° F. or higher, and down to cryogenic temperatures, defined as below −150° F., testing that has heretofore been generally unavailable at such extremes;

Apparatus allows determining physical properties of samples submerged in liquids, which also has heretofore been generally unavailable;

Apparatus provides valuable additional information on physical properties of useful pairs of materials of interest, at room temperature and also at temperature extremes, such information presently being generally unavailable in current literature; and Apparatus allows determining physical properties of samples with continuous rotation in one direction, or with reciprocating action of the sample materials, for one or many cycles, as they are pressed together.

Although the description above contains many specificities, these should not be construed as limiting the scope of the invention but as merely providing illustrations of some of the exemplary embodiments. Therefore, it will be appreciated that the scope of protection afforded by the claims fully encompasses other embodiments, and accordingly not to be unduly limited. All structural, and functional equivalents to the elements of the above-described embodiment that are known to those of ordinary skill in the art are intended to be encompassed. Moreover, it is not necessary for a device or method to address each and every problem described herein or sought to be solved by the present technology.

What is claimed is:

1. An apparatus arranged to determine physical properties between materials as they are moved relative to each other, said apparatus comprising:

a first member arranged to secure a first test sample;

a second member arranged to secure a second test sample, said first and second members being arranged for relative motion with respect to each other and allowing contact between surfaces of said first and second test samples; and a controllable drive unit arranged to linearly drive at least one of said members toward the other with a controlled magnitude of thrust and to rotate at least one of said members with respect to the other with a controlled magnitude of torque, wherein said first member is hollow and extends along a longitudinal axis and said second member is coaxially received within said first member in an arrangement which permits movement along said axis and rotation about said axis.

2. An apparatus as in claim 1, wherein said drive unit comprises a controllable linear drive unit and a controllable rotational drive unit arranged to apply said controlled magnitudes of thrust and torque, respectively.

3. An apparatus as in claim 1, wherein said first and second members respectively include first and second test sample holders at end portions thereof distal with respect to said drive unit.

4. An apparatus as in claim 3, wherein said distal end portions of said members are adapted to project into an environmental control chamber that does not contain said drive unit.

5. An apparatus as in claim 4, wherein said an environmental control chamber (a) applies non-room temperature to said distal end portions of said members, or (b) immerses said distal end portions of said members to liquid, or (a) and (b).

6. An apparatus as in claim 3, further comprising thermal impediment adapted to impede heat transfer between said distal end portions of said members and said drive unit.

7. An apparatus as in claim 3, wherein said second member is slidably and rotatably received within said first member, said apparatus further comprising a drive shaft axially aligned with and coupled to said second member, said drive shaft also being coupled to said drive unit, wherein said thrust and said torque from said drive unit are applied to said second member through said drive shaft.

8. An apparatus as in claim 7, further comprising a frame assembly arranged to provide support to said members and drive unit, wherein a proximal end portion of said first member is fixedly coupled to said frame assembly in an arrangement that fixes said first test sample holder at said distal end portion of said first member with respect to said frame assembly.

9. An apparatus as in claim 8, further comprising thermal impediment located between said first member and said frame assembly, said thermal impediment having a lower thermal conductivity than said first member and said frame assembly.

10. An apparatus as in claim 9, wherein said thermal impediment includes a first gasket at a distal end portion thereof coupled to a portion of said first member and a second gasket at a proximal end portion thereof coupled to said frame assembly, said first and second gaskets having lower thermal conductivity than said first member and said frame assembly.

11. An apparatus as in claim 1, further comprising an attachment arranged to allow an externally applied torque to rotate at least one of said members with respect to the other while said test samples are secured therein and are in forced contact with each other due to the thrust applied by said linear drive unit.

12. An apparatus as in claim 1, wherein at least one of said magnitudes of thrust and torque forces applied by said drive unit is adjustably controllable.

13. An apparatus as in claim 1, wherein said drive unit is adapted to (a) continuously rotate said at least one member with respect to the other over 360° and (b) reciprocally rotate said at least one member with respect to the other over an arc of less than 360°.

14. An apparatus as in claim 1, wherein said members are respectively adapted to hold cylindrical test samples so that end surfaces of said test samples are engaged when secured by their respective members and brought into contact with each other through said drive unit.

15. An apparatus as in claim 14, wherein said engaging end surface of at least one of said test samples includes a recess at a center portion thereof.

16. An apparatus arranged to determine physical properties between materials as they are moved relative to each other, said apparatus comprising:
  a first member arranged to secure a first test sample;
  a second member arranged to secure a second test sample, said first and second members being arranged for relative motion with respect to each other and allowing contact between surfaces of said first and second test samples; and
  a controllable drive unit arranged to linearly drive at least one of said members toward the other with a controlled magnitude of thrust and to rotate at least one of said members with respect to the other with a controlled magnitude of torque,
  wherein said first member comprises a first elongated hollow pipe with means for fixedly securing said first test sample at a distal end portion thereof and with means for fixedly coupling a proximal end portion thereof to a frame assembly of said apparatus,
  wherein said second member comprises a second elongated pipe with means for fixedly securing said second test sample at a distal end portion thereof, said second pipe being slidably and rotatably received within said first pipe and arranged to permit contact between surfaces of said first and second test samples,
  wherein said controllable drive unit comprises means for longitudinally and rotationally driving a proximal end portion of said second pipe with respect to said first pipe and to effect an adjustably controlled magnitude of linear thrust and rotational torque to be applied to said contacting surfaces of said test samples when said test samples are respectively secured at said respective distal end portions of said pipes,
  wherein said distal ends of said pipes extend away from said frame assembly,
  wherein said means for driving are disposed toward said proximal ends of said pipes, and
  wherein said apparatus further comprises means for impeding heat transfer between said distal end portions of said pipes and said means for driving, wherein said distal end portions of said pipes project into an environmental control unit that does not contain said means for driving.

17. An apparatus as in claim 16, further comprising means for coupling said second pipe to said means for driving to effect a controlled movement of said second pipe with respect to said first pipe.

18. An apparatus as in claim 16, further comprising means allowing an external torque device to rotate said second pipe with respect said first pipe when said test samples are respectively secured at said distal end portions of said pipes and are in contact with each other due to said linear thrust.

19. An apparatus as in claim 16, wherein said means for driving includes means for (a) continuously rotating said second pipe through 360° and (b) reciprocally rotating said second pipe through an arc of less than 360°.

20. A method for determining physical properties between materials using said apparatus of claim 16, said method comprising:
  securing said first test sample to said distal end portion of said first elongated hollow member of said apparatus;
  securing said second test sample to said distal end of said second elongated member of said apparatus, said second member being slidably and rotatably received within said first member;
  longitudinally moving at least one of said members toward the other to effect contact between said test samples with a controlled magnitude of linear thrust using said controllable drive unit of said apparatus;
  rotating at least one of said members with respect to the other to effect sliding rotational motion between said contacting test samples with a controlled magnitude of rotational torque said controllable drive unit; and
  projecting said distal end portions of said members into an environmentally controlled unit.

21. A method as in claim 20, further comprising impeding heat transfer between said members and said drive unit using a thermal impediment.

22. A method as in claim 20, wherein said step of rotating comprises
  (a) continuously rotating said at least one member with respect to the other over 360°, or
  (b) reciprocally rotating said at least one member with respect to the other over an arc of less than 360°, or
  (a) and (b).

23. A method as in claim 20, further comprising at least one of:
   measuring magnitudes of said linear thrust and rotational torque required to rotate said at least one test sample while being subjected to such linear thrust; and
   measuring a reduction in length of said at least one test sample caused by relative movement between the test samples while under load.

24. A method as in claim 20, further comprising forming a recess in a center portion of an engaging end surface of at least one cylindrically shaped test sample.

25. A method as in claim 24, further comprising coating at least one material of interest to an engaging end surface of at least one cylindrically shaped test sample.

26. An apparatus arranged to determine physical properties between materials as they are moved relative to each other, said apparatus comprising:
   a first member arranged to secure a first test sample;
   a second member arranged to secure a second test sample, said first and second members being arranged for relative motion with respect to each other and allowing contact between surfaces of said first and second test samples; and
   a controllable drive unit arranged to linearly drive at least one of said members toward the other with a controlled magnitude of thrust and to rotate at least one of said members with respect to the other with a controlled magnitude of torque,
   wherein said first member comprises:
      a length of fixed metal pipe with integral flange at one end, said fixed pipe being positioned horizontally by attachment of said flange to a first vertical supporting metal plate;
      two transversely aligned holes through other end of said fixed pipe, one through the top and one through the bottom thereof; and
      a first close fitting metal pin disposed in said transverse holes in said fixed pipe,
   wherein said second member comprises:
      a second length of metal pipe rotatably disposed inside said first pipe and fitting closely thereto within;
      two transversely aligned holes through one end of said second pipe, one through the top and one through the bottom thereof, at an end proximate to said one end of said fixed pipe having said transversely aligned holes; and
      a second close fitting metal pin disposed in said transversely aligned holes in the one end of said second pipe, and
   wherein said controllable drive unit comprises a rotatable drive shaft, a rotary actuator, and a diaphragm actuator,
      said drive shaft attaching to said second pipe at the end opposite the end having said transverse through holes,
      said drive shaft passing through said first vertical plate,
      said drive shaft passing slidably through the bore of said rotary actuator,
      said rotary actuator being fixed to said first vertical plate,
      said drive shaft being rotatable by said rotary actuator via key and keyways in said shaft and said bore,
      said shaft extending to a thrust bearing in a housing,
      said housing attached through a coupling to a pneumatic diaphragm actuator,
      said diaphragm actuator being fixed to a second vertical metal plate that is parallel to said first vertical plate and fixed thereto, and
      said diaphragm actuator being supplied with adjustable air supply.

27. An apparatus as in claim 26, wherein said rotary actuator is a pneumatic or an electric actuator capable of
   (a) reciprocating through a 90° arc, or
   (b) continuously rotating, or
   (a) and (b).

28. An apparatus as in claim 26, wherein said first test sample is a first non-rotatable sample coupon to be tested, in the form of a cylinder with a centrally located transverse hole passing therethrough, is disposed in axial alignment in the one end of said fixed pipe, held in position therein by said first metal pin passing through said transverse holes in said fixed pipe and in said first sample coupon, said second test sample is a second rotatable sample coupon being disposed in axial alignment in said second pipe, held in position there in like manner by said second metal pin, whereby ends of said first non-rotatable sample coupon and of said second rotatable sample coupon are in forced contact through the application of pneumatic pressure to said diaphragm actuator, creating said forced contact through force from said diaphragm actuator through said bearing housing to said thrust bearing along said drive shaft to said second length of pipe to said second strong metal pin to said second rotatable sample coupon.

29. An apparatus as in claim 28, wherein said first sample coupon is held in fixed position, and said second sample coupon is held in forced contact against said first sample coupon and is rotated against said first sample coupon.

30. An apparatus as in claim 29, wherein said forced contact is adjustable by virtue of adjustable pneumatic pressure to said diaphragm actuator.

31. An apparatus as in claim 29 wherein the rotation is a reciprocating 90° rotation or a continuous rotation.

32. An apparatus as in claim 26, wherein said fixed pipe integral flange is separated from said first vertical plate by a first ceramic washer and a pipe spool and a second ceramic washer disposed between said fixed pipe integral flange and said first vertical plate.

33. An apparatus as in claim 28, wherein the end of the said fixed pipe that contains the sample coupons to be tested is inserted into an oven or a cold box.

34. An apparatus as in claim 28, wherein the one end of said fixed pipe that contains the sample coupons to be tested is immersed in a liquid during testing.

35. An apparatus as in claim 28, wherein the torque required to turn said second rotatable test coupon against said first fixed test coupon is measured with a torque wrench attached to said rotatable drive shaft, thereby to calculate the coefficient of friction between said first and second sample coupons.

36. An apparatus as in claim 26, wherein the length of the test coupons before and after testing is measured to indicate WR of the materials of the test coupons.

* * * * *